US007223852B2

United States Patent
Tschopp et al.

(10) Patent No.: US 7,223,852 B2
(45) Date of Patent: May 29, 2007

(54) NUCLEIC ACIDS ENCODING TRAIN-R: A CYSTEINE RICH MEMBER OF THE TNF-RECEPTOR FAMILY

(75) Inventors: Jurg Tschopp, Epalinges (CH); Catherine Hession, Hingham, MA (US)

(73) Assignees: Biogen IDEC MA Inc., Cambridge, MA (US); Apoxis S.A., Epalinges (CH)

( * ) Notice: Subject to any disclaimer, the term of this patent is extended or adjusted under 35 U.S.C. 154(b) by 673 days.

(21) Appl. No.: 10/303,502

(22) Filed: Nov. 22, 2002

(65) Prior Publication Data

US 2003/0219860 A1 Nov. 27, 2003

Related U.S. Application Data

(63) Continuation of application No. 09/522,436, filed on Mar. 9, 2000, now abandoned, which is a continuation-in-part of application No. PCT/US98/19030, filed on Sep. 11, 1998.

(60) Provisional application No. 60/084,422, filed on May 6, 1998, provisional application No. 60/058,631, filed on Sep. 12, 1997.

(51) Int. Cl.
C07H 21/04 (2006.01)
C12P 21/06 (2006.01)
C12N 1/20 (2006.01)
C12N 15/00 (2006.01)
C12N 15/74 (2006.01)

(52) U.S. Cl. ................. 536/23.5; 435/69.1; 435/252.3; 435/320.1; 435/325; 435/471

(58) Field of Classification Search ................ None
See application file for complete search history.

(56) References Cited

U.S. PATENT DOCUMENTS

| 5,225,538 A | 7/1993 | Capon et al. | |
|---|---|---|---|
| 2002/0068696 A1 | 6/2002 | Wood et al. | |
| 2003/0219860 A1* | 11/2003 | Tschopp et al. | ............ 435/69.1 |
| 2004/0142423 A1* | 7/2004 | Tada et al. | ................. 435/69.1 |
| 2006/0058223 A1 | 3/2006 | Mi et al. | |

FOREIGN PATENT DOCUMENTS

| EP | 0990703 A1 | | 4/2000 |
|---|---|---|---|
| WO | WO 94/04679 | | 3/1994 |
| WO | WO 98/01554 | | 1/1998 |
| WO | WO 98/38304 | * | 3/1998 |
| WO | WO 99/11791 | | 3/1999 |
| WO | WO 99/13078 | | 3/1999 |
| WO | WO 99/20644 | | 4/1999 |
| WO | WO 99/33967 | | 7/1999 |
| WO | WO 99/33980 | | 7/1999 |
| WO | WO 99/37818 | | 7/1999 |
| WO | WO 00/01817 | | 1/2000 |
| WO | WO 2006/017673 A2 | | 1/2000 |
| WO | WO 00/49149 | | 8/2000 |
| WO | WO 00/53758 | | 9/2000 |
| WO | WO 01/38526 | | 5/2001 |
| WO | WO 01/58954 | | 8/2001 |
| WO | WO 01/68848 | | 9/2001 |
| WO | WO 01/93983 | | 12/2001 |
| WO | WO 02/00690 | | 1/2002 |
| WO | WO 02/08284 | | 1/2002 |
| WO | WO 02/08288 | | 1/2002 |
| WO | WO 03/013578 | | 2/2003 |
| WO | WO 2005/058028 | | 6/2005 |

OTHER PUBLICATIONS

Skolnick et al. Trends in Biotech. 18:34-39, 2000.*
Bork P. Genome Research 10:398-400, 2000.*
Doerks et al. Trends in Genetics 14:248-250, 1998.*
Smith et al. Nature Biotechnology 15:1222-1223, 1997.*
Brenner SE. Trends in Genetics 15:132-133, 1999.*
Bork, et al. Trends in Genetics 12:425-427, 1996.*
Aggarwal et al., "Tumor Necrosis Factors: Developments During the Last Decade," *Eur. Cytokine Netw*, 7:93-124 (1996).
Bazzoni et al., "The Tumor Necrosis Factor Ligand and Receptor Families," *N Engl. J. Med.*, 334:1717-1725 (1996).
Bork, "Powers and Pitfalls in Sequence Analysis: The 70% Hurdle," *Genome Res.* 10:39-400 (2000).
Eason et al., "Evaluation of Recombinant Human Soluble Dimeric Tumor Necrosis Factor Receptor for Prevention of OKT3-associated Acute Clinical Syndrome," *Transplantation*, 61:224-228 (1996).
Eggermont et al., "Isolated Limb Perfusion with High-Dose Tumor Necrosis Factor-Alpha in Combination With Interferon-Gamma and Melphalan for Nonresectable Extremity Soft Tissue Sarcomas: A Multicenter Trial," *J. Clin. Oncol.*, 14:2653-2665 (1996).
Feldmann et al., "Role of Cytokines in Rheumatoid Arthritis," *Annu. Rev. Immunol.*, 14:397-440 (1996).
Green et al., "Fas-Ligand: Privilege And Peril.," *Proc. Natl. Acad. Sci. USA*, 94:5986-5990 (1997).
Banner, D.W., et al., "Crystal Structure of the Soluble Human 55 kd TNF Receptor-Human TNFβ Complex: Implications for TNF Receptor Activation," *Cell* 73:431-445, Cell Press (1993).
Bodmer, J.-L., et al., "The molecular architecture of the TNF superfamily," *Trends Biomed. Sci.* 27:19-26, Elsevier Science Ltd. (Jan. 2002).
Eby, M.T., et al., "TAJ, a Novel Member of the Tumor Necrosis Factor Receptor Family, Activates the c-Jun N-terminal Kinase Pathway and Mediates Caspase-independent Cell Death," *J. Biol. Chem.* 275:15336-15342, The American Society for Biochemistry and Molecular Biology, Inc. (May 2000).

(Continued)

*Primary Examiner*—Robert S. Landsman
(74) *Attorney, Agent, or Firm*—Sterne, Kessler, Goldstein & Fox, P.L.L.C.

(57) ABSTRACT

The present invention relates to novel receptors in the TNF family. A novel receptor has been identified, referred to herein as TRAIN. The invention relates to DNA sequences encoding TRAIN receptors. The invention also contemplates recombinant DNAs comprising a sequence encoding TRAIN receptors or fragments thereof, as well as hosts with stably integrated TRAIN-R sequences introduced into their genome, or possessing episomal elements.

12 Claims, 5 Drawing Sheets

OTHER PUBLICATIONS

Hisaoka, T., et al., "Expression of a member of tumor necrosis factor receptor superfamily, TROY, in the developing mouse brain," *Develop. Brain Res. 143*:105-109, Elsevier Science B.V. (Jun. 2003).

Kojima, T., et al., "TROY, a Newly Identified Member of the Tumor Necrosis Factor Receptor Superfamily, Exhibits a Homology with Edar and Is Expressed in Embryonic Skin and Hair Follicles," *J. Biol. Chem. 275*:20742-20747, The American Society for Biochemistry and Molecular Biology, Inc. (Jul. 2000).

Mandemakers, W.J. and Barres, B.A., "Axon Regeneration: It's Getting Crowded at the Gates of TROY," *Curr. Biol. 15*:R302-R305, Cell Press (Apr. 2005).

Robertson, N.G., et al., "Isolation of Novel and Known Genes from a Human Fetal Cochlear cDNA Library Using Subtractive Hybridization and Differential Screening," *Genomics 23*:42-50, Academic Press, Inc. (1994).

Shao, Z., et al., "TAJ/TROY, an Orphan TNF Receptor Family Member, Binds Nogo-66 Receptor 1 and Regulates Axonal Regeneration," *Neuron 45*:353-359, Elsevier Inc. (Feb. 2005).

Wang, Y., et al., "An alternative form of paraptosis-like cell death, triggered by TAJ/TROY and enhanced by PDCD5 overexpression," *J. Cell Sci. 117*:1525-1532, The Company of Biologists (Mar. 2004).

Wilson, C.A. and Browning, J.L., "Death of HT29 adenocarcinoma cells induced by TNF family receptor activation is caspase-independent and displays features of both apoptosis and necrosis," *Cell Death Diff. 9*:1321-1333, Nature Publishing Group (Dec. 2002).

NCBI Entrez, Accession No. AAF71828, Eby, M.T., et al. (May 25, 2000).

NCBI Entrez, Accession No. NP_061117, Clark, H.F., et al. (Jul. 5, 2000).

NCBI Entrez, Accession No. BAB03269, Kojima, T., et al. (Jul. 22, 2000).

NCBI Entrez, Accession No. AAK28396, Chaudhary, D. and Long A.J. (Apr. 2, 2001).

NCBI Entrez, Accession No. Q9NS68, Eby, M.T., et al. (May 30, 2002).

NCBI Entrez, Accession No. NM_148957, Clark, H.F., et al. (Sep. 20, 2002).

NCBI Entrez, Accession No. AY358888, Clark, H.F., et al. (Oct. 1, 2003).

NCBI Entrez, Accession No. CAH70838, Pearce, A. (Nov. 9, 2004).

NCBI Entrez, Accession No. BC047321, Strausberg, R.L., et al. (Mar. 3, 2003).

Mikayama et al., "Molecular Cloning and Functional Expression of a cDNA Encoding Glycosylation-Inhibiting Factor," *Proc. Natl. Acad. Sci. USA*, 90:10056-10060 (1993).

Skolnick et al., "From Genes to Proteins Structure and Function: Novel Applications of Computational Approaches in the Genomic Area," *Trends Biotechnol.*, 18:34-39 (2000).

Smith, "Virus Strategies for Evasion of the Host Response to Infection," *Trends Microbiol.*, 2:81-88 (1994).

Smith et al., "CD30 Antigen, a Marker for Hodgkin's Lymphoma, is a Receptor Whose Ligand Defines an Emerging Family of Cytokines with Homology to TNF," *Cell*, 73:1349-1360 (1993).

Smith et al., "The TNF Receptor Superfamily of Cellular and Viral Proteins: Activation, Costimulation, and Death," *Cell*, 76:959-962 (1994).

van Dullemen et al., "Treatment of Crohn's Disease with Anti-Tumor Necrosis Factor Chimeric Monoclonal Antibody (cA2)," *Gastroenterology*, 109:129-135 (1995).

* cited by examiner

```
   1  GAATTCCGGG GGAGGTGCAC GGTGTGCACG CTGGACTGGA CCCCCCATGC
  51  AACCCCGCGC CCTGCGCCTT AACCAGGACT GCTCCGCGCG CCCCTGAGCC
 101  TCGGCTCCG  GCCCGGACCT GCAGCCTCCC AGGTGGCTGG GAAGAACTCT
 151  CCAACAATAA ATACATTTGA TAAGAAAGAT GGCTTTAAAA GTGCTACTAG
 201  AACAAGAGAA AACGTTTTTC ACTCTTTTAG TATTACTAGG CTATTTGTCA
 251  TGTAAAGTGA CTTGTGAATC AGGAGACTGT AGACAGCAAG AATTCAGGGA
 301  TCGGTCTGGA AACTGTGTTC CCTGCAACCA GTGTGGGCCA GGCATGGAGT
 351  TGTCTAAGGA ATGTGGCTTC GGCTATGGGG AGGATGCACA GTGTGTGACG
 401  TGCCGGCTGC ACAGGTTCAA GGAGGACTGG GGCTTCCAGA AATGCAAGCC
 451  CTGTCTGGAC TGCGCAGTGG TGAACCGCTT TCAGAAGGCA AATTGTTCAG
 501  CCACCAGTGA TGCCATCTGC GGGGACTGCT TGCCAGGATT TTATAGGAAG
 551  ACGAAACTTG TCGGCTTTCA AGACATGGAG TGTGTGCCTT GTGGAGACCC
 601  TCCTCCTCCT TACGAACCGC ACTGTGCCAG CAAGGTCAAC CTCGTGAAGA
 651  TCGCGTCCAC GGCCTCCAGC CCACGGGACA CGGCGCTGGC TGCCGTTATC
 701  TGCAGCGCTC TGGCCACCGT CCTGCTGGCC CTGCTCATCC TCTGTGTCAT
 751  CTATTGTAAG AGACAGTTTA TGGAGAAGAA ACCCAGCTGG TCTCTGCGGT
 801  CGCAGGACAT TCAGTACAAC GGCTCTGAGC TGTCGTGTTT TGACAGACCT
 851  CAGCTCCACG AATATGCCCA CAGAGCCTGC TGCCAGTGCC GCCGTGACTC
 901  AGTGCAGACC TGCGGGCCGG TGCGCTTGCT CCCATCCATG TGCTGTGAGG
 951  AGGCCTGCAG CCCCAACCCG GCGACTCTTG GTTGTGGGT  GCATTCTGCA
1001  GCCAGTCTTC AGGCAAGAAA CGCAGGCCCA GCCGGGGAGA TGGTGCCGAC
1051  TTTCTTCGGA TCCCTCACGC AGTCCATCTG TGGCGAGTTT TCAGATGCCT
1101  GGCCTCTGAT GCAGAATCCC ATGGGTGGTG ACAACATCTC TTTTTGTGAC
1151  TCTTATCCTG AACTCACTGG AGAAGACATT CATTCTCTCA ATCCAGAACT
1201  TGAAAGCTCA ACGTCTTTGG ATTCAAATAG CAGTCAAGAT TTGGTTGGTG
1251  GGGCTGTTCC AGTCCAGTCT CATTCTGAAA ACTTTACAGC AGCTACTGAT
1301  TTATCTAGAT ATAACAACAC ACTGGTAGAA TCAGCATCAA CTCAGGATGC
1351  ACTAACTATG AGAAGCCAGC TAGATCAGGA GAGTGGCGCT GTCATCCACC
1401  CAGCCACTCA GACGTCCCTC CAGGAAGCTT AAAGAACCTG CTTCTTTCTG
1451  CAGTAGAAGC GTGTGCTGGA ACCCAAAGAG TACTCCTTTG TTAGGCTTAT
1501  GGACTGAGCA GTCTGGACCT TGCATGGCTT CTGGGGCAAA AATAAATCTG
1551  AACCAAACTG ACGGCATTTG AAGCCTTTCA GCCAGTTGCT TCTGAGCCAG
1601  ACCAGCTGTA AGCTGAAACC TCAATGAATA ACAAGAAAAG ACTCCAGGCC
1651  GACTCATGAT ACTCTGCATC TTTCCTACAT GAGAAGCTTC TCTGCCACAA
1701  AAGTGACTTC AAAGACGGAT GGGTTGAGCT GGCAGCCTAT GAGATTGTGG
1751  ACATATAACA AGAAACAGAA ATGCCCTCAT GCTTATTTTC ATGGTGATTG
1801  TGGTTTTACA AGACTGAAGA CCCAGAGTAT ACTTTTTCTT TCCAGAAATA
1851  ATTTCATACC GCCTATGAAA TATCAGATAA ATTACCTTAG CTTTTATGTA
1901  GAATGGGTTC AAAAGTGAGT GTTTCTATTT GAGAAGGACA CTTTTTCATC
1951  ATCTAAACTG ATTCGCATAG GTGGTTAGAA TGGCCCTCAT ATTGCCTGCC
2001  TAAATCTTGG GTTTATTAGA TGAAGTTTAC TGAATCAGAG GAATCAGACA
2051  GAGGAGGATA GCTCTTTCCA GAATCCACAC TTCTGACCTC AGCCTCGGTC
2101  TCATGAACAC CCGCTGATCT CAGGAGAACA CCTGGCTAG  GGAATGTGGT
2151  CGAGAAAGGG CAGCCCATTG CCCAGAATTA ACACA
```

FIG. 1

```
      Gap Weight:   3.000      Average Match:   0.540
   Length Weight:   0.100   Average Mismatch:  -0.396

Quality: 272.2              Length:    214
           Ratio:   1.272              Gaps:      0
Percent Similarity:  86.449    Percent Identity:  81.776

1 MALKVLLEQEKTFFTLLVLLGYLSCKVTCESGDCRQQEFRDRSGNCVPCN 50
    ||||||  : ..:|. :::| .|.|||.||.||||||||:||||||| |.
  1 MALKVLPLHRTVLFAAILFLLHLACKVSCETGDCRQQEFKDRSGNCVLCK 50

51 QCGPGMELSKECGFGYGEDAQCVTCRLHRFKEDWGFQKCKPCLDCAVVNR 100
    ||||||||||||||||||||||.|| |||||||||||||||| |||:|||
 51 QCGPGMELSKECGFGYGEDAQCVPCRPHRFKEDWGFQKCKPCADCALVNR 100

101 FQKANCSATSDAICGDCLPGFYRKTKLVGFQDMECVPCGDPPPPYEPHCA 150
    ||:|||| ||||:||||||||||||||||||||||||||||||||||||.
101 FQRANCSHTSDAVCGDCLPGFYRKTKLVGFQDMECVPCGDPPPPYEPHCT 150

151 SKVNLVKIASTASSPRDTALAAVICSALATVLLALLILCVIYCKRQFMEK 200
    ||||||||.||.||||||||||||||||||||||||||||||||||||||
151 SKVNLVKISSTVSSPRDTALAAVICSALATVLLALLILCVIYCKRQFMEK 200

201 KPSWSLRSQDIQYN 214
    ||| .|.|  :  .
201 KPSCKLPSLCLTVK 214
```

FIG. 2

```
  1 GAATTCCAAA TGCTAAAACC TAGTTCTTTA TTCATCTATA AGGTATTTTG
 51 TCGTTTAAGT TTCAATAAAA ATGCCGAAGA CCACTGACTT TATATTCCCC
101 CACCTGCACC CCCACCCCAA TATAGAAGAA GTGCACTGAG AAGCATCTGC
151 AAAGTTAGCT TTAGGGGAAT TGATATTTCT TAAGTGTCCA CTGCTTCCTC
201 TTCAAAAATG TGTCTACCTA AGATACTATT ATTTAAGCCT CTGTGTACTT
251 TTAACCGTAG AACTGGTAAT GGAGACTGCT GGTAATTTAT GACCACAACT
301 GTAAGCTTAG ATGAAAGAGT TAACAAGGAG TATTTTCCTT TCTCTTCTAG
351 ATTTTATAGG AAGACGAAAC TTGTCGGCTT TCAAGACATG GAGTGTGTGC
401 CTTGTGGAGA CCCTCCTCCT CCTTACGAAC CGCACTGTGA GTGAACGCAA
451 CACAGGCAGA GCCAAGGGGA CGCCTGGCCT TTTGAAAAAG TTTAAATTTG
501 TAAACGTTTC TTCTCTGGCA GATGGAGCCA AATCTGTCTC TCCTGTGGGG
551 TGTACAGTGT GTCCTCTTTA ATCAGGCTTC TGGCAGGACA GAAAGTCCCT
601 TTGTTCTGTG CCTCAGTCAG CAAACCGGTC CCAGGGATTT GAATCTCAGA
651 GTGGAGTGCA GACATTTTGC CACTGCTCAG CTCCTTCTGA AGCCTTCCCT
701 GGCACCCTGG GTCTGTAATT CAGGCCACTT TGAATAACCA GGCGGCTCAC
751 ATCCTCACTC TTAGGTCTTC GTGCCCTGGC CCATGAATT C
```

MALKVLLEQEKTFFTLLVLLGYLSCKVTCESGDCRQQEFRDRSGNCVPCNQCGPGMELSKECGFGYGE
DAQCVTCRLHRFKEDWGFQKCKPCLDCAVVNRFQKANCSATSDAICGDCLPGFYRKTKLVGFQDMECV
PCGDPPPPYEPHCASKVNLVKIASTASSPRDTALAAVICSALATVLLALLILCVIYCKRQFMEKKPSW
SLRSQDIQYNGSELSCFDRPQLHEYAHRACCQCRRDSVQTCGPVRLLPSMCCEEACSPNPATLGCGVH
SAASLQARNAGPAGEMVPTFFGSLTQSICGEFSDAWPLMQNPMGGDNISFCDSYPELTGEDIHSLNPE
LESSTSIDSNSSQDLVGGAVPVQSHSENFTAATDLSRYNNTLVESASTQDALTMRSQLDQESGAVIHP
ATQTSLQEA

FIG 5

FYRKTKLVGFQDMECVPCGDPPPPYEPHCE

SEQUENCE LISTING

<160> NUMBER OF SEQ ID NOS: 9

<210> SEQ ID NO 1
<211> LENGTH: 150
<212> TYPE: PRT
<213> ORGANISM: MUS MUSCULUS

<400> SEQUENCE: 1

```
Met Ala Leu Lys Val Leu Pro Leu His Arg Thr Val Leu Phe Ala Ala
 1               5                  10                  15

Ile Leu Phe Leu Leu His Leu Ala Cys Lys Val Ser Cys Glu Thr Gly
                20                  25                  30

Asp Cys Arg Gln Gln Glu Phe Lys Asp Arg Ser Gly Asn Cys Val Leu
            35                  40                  45

Cys Lys Gln Cys Gly Pro Gly Met Glu Leu Ser Lys Glu Cys Gly Phe
        50                  55                  60

Gly Tyr Gly Glu Asp Ala Gln Cys Val Pro Cys Arg Pro His Arg Phe
65                  70                  75                  80

Lys Glu Asp Trp Gly Phe Gln Lys Cys Lys Pro Cys Ala Asp Cys Ala
                85                  90                  95

Leu Val Asn Arg Phe Gln Arg Ala Asn Cys Ser His Thr Ser Asp Ala
            100                 105                 110

Val Cys Gly Asp Cys Leu Pro Gly Phe Tyr Arg Lys Thr Lys Leu Val
        115                 120                 125

Gly Phe Gln Asp Met Glu Cys Val Pro Cys Gly Asp Pro Pro Pro Pro
    130                 135                 140

Tyr Glu Pro His Cys Glu
145                 150
```

<210> SEQ ID NO 2
<211> LENGTH: 214
<212> TYPE: PRT
<213> ORGANISM: Mus musculus

<400> SEQUENCE: 2

```
Met Ala Leu Lys Val Leu Pro Leu His Arg Thr Val Leu Phe Ala Ala
 1               5                  10                  15

Ile Leu Phe Leu Leu His Leu Ala Cys Lys Val Ser Cys Glu Thr Gly
            20                  25                  30

Asp Cys Arg Gln Gln Glu Phe Lys Asp Arg Ser Gly Asn Cys Val Leu
        35                  40                  45

Cys Lys Gln Cys Gly Pro Gly Met Glu Leu Ser Lys Glu Cys Gly Phe
    50                  55                  60

Gly Tyr Gly Glu Asp Ala Gln Cys Val Pro Cys Arg Pro His Arg Phe
 65                  70                  75                  80

Lys Glu Asp Trp Gly Phe Gln Lys Cys Lys Pro Cys Ala Asp Cys Ala
                85                  90                  95

Leu Val Asn Arg Phe Gln Arg Ala Asn Cys Ser His Thr Ser Asp Ala
            100                 105                 110

Val Cys Gly Asp Cys Leu Pro Gly Phe Tyr Arg Lys Thr Lys Leu Val
        115                 120                 125

Gly Phe Gln Asp Met Glu Cys Val Pro Cys Gly Asp Pro Pro Pro Pro
130                 135                 140

Tyr Glu Pro His Cys Thr Ser Lys Val Asn Leu Val Lys Ile Ser Ser
145                 150                 155                 160

Thr Val Ser Ser Pro Arg Asp Thr Ala Leu Ala Ala Val Ile Cys Ser
                165                 170                 175

Ala Leu Ala Thr Val Leu Leu Ala Leu Leu Ile Leu Cys Val Ile Tyr
            180                 185                 190

Cys Lys Arg Gln Phe Met Glu Lys Lys Pro Ser Cys Lys Leu Pro Ser
        195                 200                 205

Leu Cys Leu Thr Val Lys
        210
```

<210> SEQ ID NO 3
<211> LENGTH: 417
<212> TYPE: PRT
<213> ORGANISM: Homo sapiens

<400> SEQUENCE: 3

```
Met Ala Leu Lys Val Leu Leu Glu Gln Glu Lys Thr Phe Phe Thr Leu
 1               5                  10                  15

Leu Val Leu Leu Gly Tyr Leu Ser Cys Lys Val Thr Cys Glu Ser Gly
            20                  25                  30

Asp Cys Arg Gln Gln Glu Phe Arg Asp Arg Ser Gly Asn Cys Val Pro
        35                  40                  45

Cys Asn Gln Cys Gly Pro Gly Met Glu Leu Ser Lys Glu Cys Gly Phe
    50                  55                  60

Gly Tyr Gly Glu Asp Ala Gln Cys Val Thr Cys Arg Leu His Arg Phe
 65                  70                  75                  80

Lys Glu Asp Trp Gly Phe Gln Lys Cys Lys Pro Cys Leu Asp Cys Ala
                85                  90                  95

Val Val Asn Arg Phe Gln Lys Ala Asn Cys Ser Ala Thr Ser Asp Ala
            100                 105                 110

Ile Cys Gly Asp Cys Leu Pro Gly Phe Tyr Arg Lys Thr Lys Leu Val
        115                 120                 125

Gly Phe Gln Asp Met Glu Cys Val Pro Cys Gly Asp Pro Pro Pro Pro
130                 135                 140
```

-continued

```
Tyr Glu Pro His Cys Ala Ser Lys Val Asn Leu Val Lys Ile Ala Ser
145                 150                 155                 160

Thr Ala Ser Ser Pro Arg Asp Thr Ala Leu Ala Ala Val Ile Cys Ser
            165                 170                 175

Ala Leu Ala Thr Val Leu Leu Ala Leu Leu Ile Leu Cys Val Ile Tyr
        180                 185                 190

Cys Lys Arg Gln Phe Met Glu Lys Lys Pro Ser Trp Ser Leu Arg Ser
    195                 200                 205

Gln Asp Ile Gln Tyr Asn Gly Ser Glu Leu Ser Cys Phe Asp Arg Pro
210                 215                 220

Gln Leu His Glu Tyr Ala His Arg Ala Cys Cys Gln Cys Arg Arg Asp
225                 230                 235                 240

Ser Val Gln Thr Cys Gly Pro Val Arg Leu Leu Pro Ser Met Cys Cys
            245                 250                 255

Glu Glu Ala Cys Ser Pro Asn Pro Ala Thr Leu Gly Cys Gly Val His
        260                 265                 270

Ser Ala Ala Ser Leu Gln Ala Arg Asn Ala Gly Pro Ala Gly Glu Met
    275                 280                 285

Val Pro Thr Phe Phe Gly Ser Leu Thr Gln Ser Ile Cys Gly Glu Phe
290                 295                 300

Ser Asp Ala Trp Pro Leu Met Gln Asn Pro Met Gly Gly Asp Asn Ile
305                 310                 315                 320

Ser Phe Cys Asp Ser Tyr Pro Glu Leu Thr Gly Glu Asp Ile His Ser
            325                 330                 335

Leu Asn Pro Glu Leu Glu Ser Ser Thr Ser Leu Asp Ser Asn Ser Ser
        340                 345                 350

Gln Asp Leu Val Gly Gly Ala Val Pro Val Gln Ser His Ser Glu Asn
    355                 360                 365

Phe Thr Ala Ala Thr Asp Leu Ser Arg Tyr Asn Asn Thr Leu Val Glu
370                 375                 380

Ser Ala Ser Thr Gln Asp Ala Leu Thr Met Arg Ser Gln Leu Asp Gln
385                 390                 395                 400

Glu Ser Gly Ala Val Ile His Pro Ala Thr Gln Thr Ser Leu Gln Glu
            405                 410                 415

Ala
```

<210> SEQ ID NO 4
<211> LENGTH: 30
<212> TYPE: PRT
<213> ORGANISM: Homo sapiens

<400> SEQUENCE: 4

```
Phe Tyr Arg Lys Thr Lys Leu Val Gly Phe Gln Asp Met Glu Cys Val
1               5                   10                  15

Pro Cys Gly Asp Pro Pro Pro Tyr Glu Pro His Cys Glu
            20                  25                  30
```

<210> SEQ ID NO 5
<211> LENGTH: 599
<212> TYPE: DNA
<213> ORGANISM: Mus musculus

<400> SEQUENCE: 5

```
ggcacgaggg cgtttggcgc ggaagtgcta ccaagctgcg aaagcgtga gtctggagca    60 cagcactggc gagtagcagg aataaacacg tttggtgaga gccatggcac tcaaggtcct   120
```

```
acctctacac aggacggtgc tcttcgctgc cattctcttc ctactccacc tggcatgtaa      180
agtgagttgc gaaaccggag attgcaggca gcaggaattc aaggatcgat ctggaaactg      240
tgtcctctgc aaacagtgcg gacctggcat ggagttgtcc aaggaatgtg gcttcggcta      300
tggggaggat gcacagtgtg tgccctgcag gccgcaccgg ttcaaggaag actggggttt      360
ccagaagtgt aagccatgtg cggactgtgc gctggtgaac cgctttcaga gggccaactg      420
ctcacacacc agtgatgctg tctgcgggga ctgcctgcca ggattttacc ggaagaccaa      480
actggttggt tttcaagaca tggagtgtgt gccctgcgga gacccacctc ctccctacga      540
accacactgt gagtgatgtg ccaagtggca gcagaccttt aaaaaaaaaa gaaaaaaaa        599

<210> SEQ ID NO 6
<211> LENGTH: 942
<212> TYPE: DNA
<213> ORGANISM: Mus musculus

<400> SEQUENCE: 6
cggcacgagg gccggcaccc cgcgccaccc cagcctcaaa ctgcagtccg gcgccgcggg       60
gcaggacaag gggaaggaat aaacacgttt ggtgagagcc atggcactca aggtcctacc      120
tctacacagg acggtgctct tcgctgccat tctcttccta ctccacctgg catgtaaagt      180
gagttgcgaa accggagatt gcaggcagca ggaattcaag gatcgatctg aaactgtgt      240 cctctgcaaa cagtgcggac ctggcatgga gttgtccaag gaatgtggct tcggctatgg      300
ggaggatgca cagtgtgtgc cctgcaggcc gcaccggttc aaggaagact ggggtttcca      360
gaagtgtaag ccatgtgcgg actgtgcgct ggtgaaccgc tttcagaggg ccaactgctc      420
acacaccagt gatgctgtct gcggggactg cctgccagga ttttaccgga agaccaaact      480
ggttggtttt caagacatgg agtgtgtgcc ctgcggagac ccacctcctc cctacgaacc      540
acactgtacc agcaaggtga accttgtgaa gatctcctcc accgtctcca gccctcggga      600
cacggcgctg gctgccgtca tctgcagtgc tctggccacg gtgctgctcg ccctgctcat      660
cctgtgtgtc atctactgca agaggcagtt catggagaag aaacccagct gtaagctccc      720
atccctctgt ctcactgtga agtgagcttg ttagcattgt cacccaagag ttctcaagac      780
acctggctga gacctaagac ctttagagca tcaacagcta cttagaatac aagatgcagg      840
aaaacgagcc tcttcaggaa tctcagggcc tcctagggat gctggcaagg ctgtgatgtc      900
tcaagctacc aggaaaaatt taagttgtt twtcccctaa aa                          942

<210> SEQ ID NO 7
<211> LENGTH: 2185
<212> TYPE: DNA
<213> ORGANISM: Homo sapiens

<400> SEQUENCE: 7
gaattccggg ggaggtgcac ggtgtgcacg ctggactgga ccccccatgc aaccccgcgc       60
cctgcgcctt aaccaggact gctccgcgcg cccctgagcc tcgggctccg gcccggacct      120
gcagcctccc agtggctggg aagaactct ccaacaataa atacatttga taagaaagat       180
ggctttaaaa gtgctactag aacaagagaa acgttttttc actctttag tattactagg       240 ctatttgtca tgtaaagtga cttgtgaatc aggagactgt agacagcaag aattcaggga      300
tcggtctgga aactgtgttc cctgcaacca gtgtgggcca ggcatggagt tgtctaagga      360
atgtggcttc ggctatgggg aggatgcaca gtgtgtgacg tgccggctgc acaggttcaa      420
ggaggactgg ggcttccaga aatgcaagcc ctgtctggac tgcgcagtgg tgaaccgctt      480
```

-continued

| | |
|---|---|
| tcagaaggca aattgttcag ccaccagtga tgccatctgc ggggactgct tgccaggatt | 540 |
| ttataggaag acgaaacttg tcggcttTca agacatggag tgtgtgcctt gtggagaccc | 600 |
| tcctcctcct tacgaaccgc actgtgccag caaggtcaac ctcgtgaaga tcgcgtccac | 660 |
| ggcctccagc ccacgggaca cggcgctggc tgccgttatc tgcagcgctc tggccaccgt | 720 |
| cctgctggcc ctgctcatcc tctgtgtcat ctattgtaag agacagttta tggagaagaa | 780 |
| acccagctgg tctctgcggt cgcaggacat tcagtacaac ggctctgagc tgtcgtgttt | 840 |
| tgacagacct cagctccacg aatatgccca cagagcctgc tgccagtgcc gccgtgactc | 900 |
| agtgcagacc tgcggggccgg tgcgcttgct cccatccatg tgctgtgagg aggcctgcag | 960 |
| ccccaacccg gcgactcttg gttgtggggt gcattctgca gccagtcttc aggcaagaaa | 1020 |
| cgcaggccca gccggggaga tggtgccgac tttcttcgga tccctcacgc agtccatctg | 1080 |
| tggcgagttt tcagatgcct ggcctctgat gcagaatccc atgggtggtg acaacatctc | 1140 |
| tttttgtgac tcttatcctg aactcactgg agaagacatt cattctctca atccagaact | 1200 |
| tgaaagctca acgtctttgg attcaaatag cagtcaagat ttggttggtg gggctgttcc | 1260 |
| agtccagtct cattctgaaa actttacagc agctactgat ttatctagat ataacaacac | 1320 |
| actggtagaa tcagcatcaa ctcaggatgc actaactatg agaagccagc tagatcagga | 1380 |
| gagtggcgct gtcatccacc cagccactca gacgtccctc caggaagctt aaagaacctg | 1440 |
| cttctttctg cagtagaagc gtgtgctgga acccaaagag tactccttTg ttaggcttat | 1500 |
| ggactgagca gtctggacct tgcatggctt ctggggcaaa aataaatctg aaccaaactg | 1560 |
| acggcatttg aagcctttca gccagttgct tctgagccag accagctgta agctgaaacc | 1620 |
| tcaatgaata caagaaaag actccaggcc gactcatgat actctgcatc tttcctacat | 1680 |
| gagaagcttc tctgccacaa aagtgacttc aaagacggat gggttgagct ggcagcctat | 1740 |
| gagattgtgg acatataaca agaaacagaa atgccctcat gcttattttc atggtgattg | 1800 |
| tggttttaca agactgaaga cccagagtat acttttctt tccagaaata atttcatacc | 1860 |
| gcctatgaaa tatcagataa attaccttag ctttTtatgta gaatgggttc aaaagtgagt | 1920 |
| gtttctattt gagaaggaca cttttTcatc atctaaactg attcgcatag gtggttagaa | 1980 |
| tggccctcat attgcctgcc taaatcttgg gtttattaga tgaagtttac tgaatcagag | 2040 |
| gaatcagaca gaggaggata gctctttcca gaatccacac ttctgacctc agcctcggtc | 2100 |
| tcatgaacac ccgctgatct caggagaaca cctgggctag ggaatgtggt cgagaaaggg | 2160 |
| cagcccattg cccagaatta acaca | 2185 |

<210> SEQ ID NO 8
<211> LENGTH: 791
<212> TYPE: DNA
<213> ORGANISM: Homo sapiens

<400> SEQUENCE: 8

| | |
|---|---|
| gaattccaaa tgctaaaacc tagttctTta ttcatctata aggtatttTg tcgtttaagt | 60 |
| ttcaataaaa atgccgaaga ccactgactt tatattcccc cacctgcacc cccacccaa | 120 |
| tatagaagaa gtgcactgag aagcatctgc aaagttagct ttaggggaat tgatatttct | 180 |
| taagtgtcca ctgcttcctc ttcaaaaatg tgtctaccta agatactatt atttaagcct | 240 |
| ctgtgtactt ttaaccgtag aactggtaat ggagactgct ggtaatttat gaccacaact | 300 |
| gtaagcttag atgaaagagt taacaaggag tattTtcctT tctcttctag attTtatagg | 360 |
| aagacgaaac ttgtcggctt tcaagacatg gagtgtgtgc cttgtggaga ccctcctcct | 420 |

```
ccttacgaac cgcactgtga gtgaacgcaa cacaggcaga gccaaggyga cgcctggcct    480
tttgaaaaag tttaaatttg taaacgtttc ttctctggca gatggagcca aatctgtctc    540
tcctgtgggg tgtacagtgt gtcctcttta atcaggcttc tggcaggaca gaaagtccct    600
ttgttctgtg cctcagtcag caaaccggtc ccagggattt gaatctcaga gtggagtgca    660
gacattttgc cactgctcag ctccttctga agccttccct ggcaccctgg gtctgtaatt    720
caggccactt tgaataacca ggcggctcac atcctcactc ttaggtcttc gtgccctggc    780
cccatgaatt c                                                         791

<210> SEQ ID NO 9
<211> LENGTH: 150
<212> TYPE: PRT
<213> ORGANISM: Homo sapiens

<400> SEQUENCE: 9

Met Ala Leu Lys Val Leu Leu Glu Gln Glu Lys Thr Phe Phe Thr Leu
  1               5                  10                  15

Leu Val Leu Leu Gly Tyr Leu Ser Cys Lys Val Thr Cys Glu Ser Gly
                 20                  25                  30

Asp Cys Arg Gln Gln Glu Phe Arg Asp Arg Ser Gly Asn Cys Val Pro
             35                  40                  45

Cys Asn Gln Cys Gly Pro Gly Met Glu Leu Ser Lys Glu Cys Gly Phe
         50                  55                  60

Gly Tyr Gly Glu Asp Ala Gln Cys Val Thr Cys Arg Leu His Arg Phe
 65                  70                  75                  80

Lys Glu Asp Trp Gly Phe Gln Lys Cys Lys Pro Cys Leu Asp Cys Ala
                 85                  90                  95

Val Val Asn Arg Phe Gln Lys Ala Asn Cys Ser Ala Thr Ser Asp Ala
                100                 105                 110

Ile Cys Gly Asp Cys Leu Pro Gly Phe Tyr Arg Lys Thr Lys Leu Val
            115                 120                 125

Gly Phe Gln Asp Met Glu Cys Val Pro Cys Gly Asp Pro Pro Pro Pro
        130                 135                 140

Tyr Glu Pro His Cys Glu
145                 150
```

NUCLEIC ACIDS ENCODING TRAIN-R: A CYSTEINE RICH MEMBER OF THE TNF-RECEPTOR FAMILY

RELATED APPLICATIONS

This is a continuation of U.S. patent application Ser. No. 09/522,436 filed Mar. 9, 2000, now abandoned, which is a continuation-in-part of PCT/US98/190390, filed Sep. 11, 1998, which claims benefit from prior U.S. provisional application No. 60/084,422, filed May 6, 1998, and U.S. provisional application No. 60/058,631 filed Sep. 12, 1997. The entire disclosure of each of the aforesaid patent applications are incorporated by reference herein.

BACKGROUND OF THE INVENTION

The present invention relates to novel receptors in the TNF family. A novel receptor has been identified, referred to herein as TRAIN.

The TNF family consists of pairs of ligands and their specific receptors referred to as TNF family ligands and TNF family receptors (Bazzoni and Beutler, 1996. N Engl J Med 334, 1717-25). The family is involved in the regulation of the immune system and possibly other non-immunological systems. The regulation is often at a "master switch" level such that TNF family signaling can result in a large number of subsequent events best typified by TNF. TNF can initiate the general protective inflammatory response of an organism to foreign invasion that involves the altered display of adhesion molecules involved in cell trafficking, chemokine production to drive specific cells into specific compartments and the priming of various effector cells. As such, the regulation of these pathways has clinical potential.

The TNF receptor family is a collection of related proteins that generally consist of an extracellular domain, a transmembrane domain and an intracellular signaling domain. The extracellular domain is built from 2-6 copies of a tightly disulphide bonded domain and is recognized on the basis of the unique arrangement of cysteine residues. Each receptor binds to a corresponding ligand although one ligand may share several receptors. In some cases, it is clear that by alternate RNA splicing, soluble forms of the receptors lacking the transmembrane region and intracellular domain exist naturally. Moreover, in nature, truncated versions of these receptors exist and the soluble inhibitory form may have direct biological regulatory roles. Clearly, viruses have used this tactic to inhibit TNF activity in their host organisms (Smith, 1994. Trends in Microbiol. 82, 81-88). These receptors can signal a number of events including cell differentiation, cell death or cell survival signals. Cell death signaling often is triggered via relatively direct links to the caspase cascade of proteases e.g. Fas and TNF receptors. Most receptors in this class can also activate NFKB controlled events.

An emerging theme in the TNF family of receptors has been the use by nature of both full length receptors with intracellular domains that transmit a signal and alternate forms which are either secreted or lack an intracellular signaling domain. These later forms can inhibit ligand signaling and hence can dampen a biological response. There are several examples of this phenomenon. First, the TNF receptor p75 is readily secreted following selective cleavage from the membrane and then acts to block the action of TNF. It is likely that nature has evolved this system to buffer TNF activity. A second example is provided by the TRIAL-TRAIL receptor system where there are 4 separate genes encoding TRAIL receptors. Two of these TRAIL-R1 and TRAIL-R2 possess intracellular domains and transduce signal. A third receptor (TRAIL-R4) has an intracellular domain yet this domain does not have all the elements found in R1 and R2, e.g. it lacks a domain capable of signaling cell death. Lastly, there is a fourth receptor TRAIL-R3, that is essentially a soluble form but remains tethered by a glycolipid linkage. Hence this receptor can bind ligand yet it is unable to transmit a signal, i.e. it is effectively a decoy receptor. A third example is provided by the osteoprotegerin (OPG) system where the OPG receptor lacks a transmembrane domain and is secreted into the medium. This receptor can block the signaling necessary to induce osteoclast differentiation possibly by binding to a ligand called RANK-L. The TRAIN system described here resembles the OPG paradigm in that a short version can be secreted that would inhibit the natural TRAIN-L (currently unknown) from binding to full length TRAIN and eliciting a signal.

The receptors are powerful tools to elucidate biological pathways via their easy conversion to immunoglobulin fusion proteins. These dimeric soluble receptor forms are good inhibitors of events mediated by either secreted or surface bound ligands. By binding to these ligands they prevent the ligand from interacting with cell associated receptors that can signal. Not only are these receptor-Ig fusion proteins useful in an experimental sense, but they have been successfully used clinically in the case of TNF-R-Ig to treat inflammatory bowel disease, rheumatoid arthritis and the acute clinical syndrome accompanying OKT3 administration (Eason et al., 1996. Transplantation 61, 224-8; Feldmann et al., 1996. Annu Rev Immunol; van Dullemen et al., 1995. Gastroenterology 109, 129-35). One can envision that manipulation of the many events mediated by signaling through the TNF family of receptors will have wide application in the treatment of immune based diseases and also the wide range of human diseases that have pathological sequelae due to immune system involvement. A soluble form of a recently described receptor, osteoprotegerin, can block the loss of bone mass and, therefore, the events controlled by TNF family receptor signaling are not necessarily limited to immune system regulation. Antibodies to the receptor can block ligand binding and hence can also have clinical application. Such antibodies are often very long-lived and may have advantages over soluble receptor-Ig fusion proteins which have shorter blood half-lives.

While inhibition of the receptor mediated pathway represents the most exploited therapeutic application of these receptors, originally it was the activation of the TNF receptors that showed clinical promise (Aggarwal and Natarajan, 1996. Eur Cytokine Netw 7, 93-124). Activation of the TNF receptors can initiate cell death in the target cell and hence the application to tumors was and still is attractive (Eggermont et al., 1996. J Clin Oncol 14, 2653-65). The receptor can be activated either by administration of the ligand, i.e. the natural pathway or some antibodies that can crosslink the receptor are also potent agonists. Antibodies would have an advantage in oncology since they can persist in the blood for long periods whereas the ligands generally have short lifespans in the blood. As many of these receptors may be expressed more selectively in tumors or they may only signal cell death or differentiation in tumors, agonist antibodies could be good weapons in the treatment of cancer. Likewise, many positive immunological events are mediated via the TNF family receptors, e.g. host inflammatory reactions, antibody production etc. and therefore agonistic antibodies could have beneficial effects in other, non-oncological applications.

Paradoxically, the inhibition of a pathway may have clinical benefit in the treatment of tumors. For example the Fas ligand is expressed by some tumors and this expression can lead to the death of Fas positive lymphocytes thus facilitating the ability of the tumor to evade the immune system. In this case, inhibition of the Fas system could then allow the immune system to react to the tumor in other ways now that access is possible (Green and Ware, 1997. Natl. Acad. Sci. USA 94, 5986-5990).

The receptors are also useful to discover the corresponding ligand as they can serve as probes of the ligand in expression cloning techniques (Smith et al., 1993. Cell 73, 1349-60). Likewise, the receptors and ligands can form in vitro binding assays that will allow the identification of inhibitory substances. Such substances can form the basis of novel inhibitors of the pathways.

BRIEF DESCRIPTION OF THE FIGURES

FIG. 1 shows the nucleotide sequences for human TRAIN receptor (SEQ ID NO: 7) from a composite of two lambda gt10 clones (GJ159 and GJ 158)

FIG. 2 shows a comparison of human TRAIN receptor (top) (residues 1-214 of SEQ ID NO: 3) and murine TRAIN receptor long (bottom) (SEQ ID NO: 2)

FIG. 3 shows the nucleotide sequences for human TRAIN receptor (SEQ ID NO: 8) from a subclone of lambda gt10 cDNA.

FIG. 4 shows the amino acid sequence (SEQ ID NO: 3) for human TRAIN corresponding to the nucleotide sequence in FIG. 1.

FIG. 5 shows the amino acid sequence (SEQ ID NO: 4) for human TRAIN corresponding to the nucleotide sequence in FIG. 3.

A. DEFINITIONS

"Homologous", as used herein, refers to the sequence similarity between sequences of molecules being compared. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

A "purified preparation" or a "substantially pure preparation" of a polypeptide, as used herein, means a polypeptide that has been separated from other proteins, lipids, and nucleic acids with which it naturally occurs. Preferably, the polypeptide is also separated from other substances, e.g., antibodies, matrices, etc., which are used to purify it.

"Transformed host" as used herein is meant to encompass any host with stably integrated sequence, i.e. TRAIN sequence, introduced into its genome or a host possessing sequence, i.e. receptor encoding episomal elements.

A "treatment", as used herein, includes any therapeutic treatment, e.g., the administration of a therapeutic agent or substance, e.g., a drug.

A "substantially pure nucleic acid", e.g., a substantially pure DNA, is a nucleic acid which is one or both of: (1) not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or (2) which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding TRAIN.

The terms "peptides", "proteins", and "polypeptides" are used interchangeably herein.

"Biologically active" as used herein, means having an in vivo or in vitro activity which may be performed directly or indirectly. Biologically active fragments of TRAIN may have, for example, 70% amino acid homology with the active site of the receptor, more preferably at least 80%, and most preferably, at least 90% homology. Identity or homology with respect to the receptor is defined herein as the percentage of amino acid residues in the candidate sequence which are identical to the TRAIN residues in SEQ. ID. NO. 3.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature.

The claimed invention relates to a novel receptor designated TRAIN-R. The amino acid sequence of murine TRAIN-R is set forth in SEQ. ID. NO. 1 (the short form) and SEQ. ID. NO. 2, (the long form). The full length amino acid sequence of human TRAIN-R is set forth in SEQ. ID. NO. 3 and FIG. 1. As shown in FIG. 1, the protein length is 417 amino acids. The predicted signal sequence runs from residues 1-25. It is believed that the mature N-terminus is at amino acid residue 26, the extracellular domain spans residues 26-173, the transmembrane domain spans residues 174-190, and the cytoplasmic domain spans residues 191-417. There is a potential N-linked glycosylation site at residue 105.

SEQ. ID. NO. 4 sets forth the amino acid sequence for the carboxy terminal 30 amino acids of a secreted form of human TRAIN-R from a subclone of lambda gt10 cDNA (GJ156). This peptide sequence features 30 amino acids that are identical to amino acids 121-149 of the composite protein shown in FIG. 1 and are identical to amino acids 121-150 of the C-terminus of murine TRAIN-R short form (secreted protein). SEQ. ID. NO 9 shows the amino acid sequence of the entire short secreted form of the human TRAIN-R based on the alternate cloned exon and by comparison to the mouse short form.

FIG. 2 shows a comparison of the first 214 amino acids of human TRAIN-R (417 a.a.) and murine TRAIN-R long (214 a.a.). As shown in the Figure, the two sequences have an identity of about 81.8%.

The TRAIN receptors of the invention may be isolated from mammalian tissues and purified to homogeneity, or isolated from cells which contain membrane-bound TRAIN- R, and purified to homogeneity. Methods for growing cells and isolating cell extracts are well known in the art, as are various cell types and growth and isolation methods. In general, any TRAIN-R can be isolated from any cell or tissue expressing this protein using a cDNA probe, isolating mRNA and transcribing the mRNA into cDNA. Thereafter, the protein can be produced by inserting the cDNA into an expression vector, such as a virus, plasmid, cosmid or other expression vector, inserting the expression vector into a cell, and proliferating the resulting cells. The TRAIN-R can then be isolated from the medium or cell extract by methods well known in the art. One skilled in the art can readily vary the vectors and cell lines and still obtain the claimed receptors. Alternatively, TRAIN receptors can be chemically synthesized using the sequences set forth in SEQ. ID. NOS. 1, 2, 3 or 4.

It is believed that murine TRAIN-R is expressed highest in brain and lung and at a lower level in liver, skeletal muscle and kidney. The expression pattern of human TRAIN-R differs in that a low level of expression has been detected in every tissue and cell line tested thus far (ubiquitous) with a significantly higher expression detected in heart, prostate, ovary, testis, peripheral blood lymphocytes (PBLs), thyroid, and adrenal gland.

Murine TRAIN-R may exist in nature as a natural soluble form as indicated in SEQ. ID. NO. 1. Human TRAIN-R may exist as a natural soluble form having the carboxy sequence indicated in SEQ. ID. NO. 4 and FIG. 3. The soluble protein should inhibit signaling by the full length TRAIN-R.

The present invention also encompasses DNA sequences which encode the murine (both long and short) and human TRAIN receptors (full length and carboxy terminus). These DNA sequences are set forth in SEQ. ID. NOS. 5, 6, 7 and 8, respectively. The human TRAIN-R sequence in SEQ. ID. NO. 7 contains 5'UTR, a complete coding region, a stop codon and some 3'UTR. FIG. 1 shows the nucleotide sequence for human TRAIN-R as derived from a composite sequence of GJ159 and GJ 158. As shown in FIG. 1, human TRAIN-R has a nucleotide sequence length of 2185, a coding region from 179-1429, and a stop codon at 1430-1432.

The human TRAIN-R sequence in SEQ. ID. NO. 8 contains intron sequence, an exon encoding the carboxy terminal 30 amino acids of a secreted form of human TRAIN-R, a stop codon and 3'UTR. As shown in FIG. 3, it is believed that the intron is at residues 1-350, the coding region at 352-441, the stop codon at 442-444 and the 3' UTR=445-791.

In other embodiments, the invention relates to sequences that have at least 50% homology with DNA sequences encoding the C terminal receptor binding domain of the ligands and hybridize to the claimed DNA sequences or fragments thereof, and which encode the TRAIN receptors having the sequences identified in SEQ. ID. NO. 1, 2, 3 or 4.

The invention in certain embodiments furthermore relates to DNA sequences encoding the TRAIN receptors where the sequences are operatively linked to an expression control sequence. Any suitable expression control sequences are useful in the claimed invention, and can easily be selected by one skilled in the art.

The invention also contemplates recombinant DNAs comprising a sequence encoding TRAIN receptors or fragments thereof, as well as hosts with stably integrated TRAIN-R sequences introduced into their genome, or possessing episomal elements. Any suitable host may be used in the invention, and can easily be selected by one skilled in the art without undue experimentation.

The claimed invention in certain embodiments encompasses recombinant TRAIN-R. One skilled in the art can readily isolate such recombinant receptors thereby providing substantially pure recombinant TRAIN-R polypeptides. Isolated receptors of the invention are substantially free of other contaminating materials of natural or endogenous origin, and contain less than about 10-15% by mass of protein contaminants residual of production processes.

Mammalian Receptors within the scope of the invention also include, but are not limited to, primate, human, murine, canine, feline, bovine, ovine, equine and porcine TRAIN-R. Mammalian Receptors can also be obtained by cross species hybridization using a single stranded cDNA derived from the human TRAIN-R. DNA sequences of the invention can be used as a hybridization probe to isolate Receptor cDNAS from other mammalian cDNA libraries.

Derivatives of the Receptors within the scope of the invention also include various structural forms of the proteins of SEQ. ID. NOS. 1, 2, 3 and 4 which retain biological activity. For example, a receptor protein may be in the form of acidic or basic salts, or may be in neutral form. Individual amino acid residues may also be modified by oxidation or reduction.

Receptor derivatives may also be used as immunogens, reagents in a receptor-based immunoassay, or as binding agents for affinity purification procedures of TRAIN ligands.

The present invention also includes TRAIN-R with or without associated native-pattern glycosylation. One skilled in the art will understand that the glycosylation pattern on the receptor may vary depending on the particular expression system used. For example, typically, expression in bacteria such as *E. coli* results in a non-glycosylated molecule. TRAIN-R derivatives may also be obtained by mutations of the receptors or their subunits. A mutant, as referred to herein, is a polypeptide homologous to a claimed Receptor but which has an amino acid sequence different from the native sequence due to a deletion, insertion or substitution.

Bioequivalent analogs of the Receptor proteins of the invention may be constructed by, for example, making various substitutions of residues or sequences or deleting terminal or internal residues or sequences not needed for biological activity. For example, often cysteine residues can be deleted or replaced with other amino acids to prevent formation of unnecessary or incorrect intramolecular disulfide bridges upon renaturation. Other approaches to mutagenesis involved modifications, for example, to enhance expression in the chosen expression system.

Soluble Receptors of the invention may comprise subunits which have been changed from a membrane bound to a soluble form. Thus, soluble peptides may be produced by truncating the polypeptide to remove, for example, the cytoplasmic tail and/or transmembrane region. Alternatively, the transmembrane domain may be inactivated by deletion, or by substitutions of the normally hydrophobic amino acid residues which comprise a transmembrane domain with hydrophilic ones. In either case, a substantially hydrophilic hydropathy profile is created which will reduce lipid affinity and improve aqueous solubility. Deletion of the transmembrane domain is preferred over substitution with hydrophilic amino acid residues because it avoids introducing potentially immunogenic epitopes. Soluble Receptors of the invention may include any number of well-known leader sequences at the N-terminus. Such a sequence would allow the peptides to be expressed and targeted to the secretion pathway in a eukaryotic system.

The invention herein provides agents, such as agonists and antagonists, directed against the claimed receptors. In certain embodiments of this invention, the agent comprises a blocking agent that comprises and antibody directed against the TRAIN-R that inhibits TRAIN receptor signaling. Preferably the antibody is a monoclonal antibody. Similarly, the claimed invention encompasses antibodies and other agents which act as agonists in the TRAIN pathways.

Inhibitory anti-TRAIN-R antibodies and other receptor blocking agents can be identified using screening methods that detect the ability of one or more agents either to bind to the TRAIN-R, or ligands thereto, or to inhibit the effects of TRAIN-R signaling on cells.

One skilled in the art will have knowledge of a number of assays that measure the strength of ligand-receptor binding and can be used to perform competition assays with putative TRAIN receptor blocking agents. The strength of the binding between a receptor and ligand can be measured using an enzyme-linked immunoadsorption assay (ELISA) or a radioimmunoassay (RIA). Specific binding may also be measured by flourescently labeling antibody-antigen complexes and performing fluorescence activated cell sorting analysis (FACS), or by performing other such immunodetection methods, all of which are techniques well-known in the art.

With any of these or other techniques for measuring receptor-ligand interactions, one skilled in the art can evaluate the ability of a blocking agent, alone or in combination with other agents, to inhibit binding of ligands to the receptor molecules. Such assays may also be used to test blocking agents or derivatives of such agents, i.e. fusions, chimeras, mutants or chemically altered forms, to optimize the ability of the agent to block receptor activation.

The receptor blocking agents of the invention in one embodiment comprise soluble TRAIN receptor molecules. Using the sequence information herein and recombinant DNA techniques well known in the art, functional fragments encoding the TRAIN receptor ligand binding domain can be cloned into a vector and expressed in an appropriate host to produce a soluble receptor molecule. Soluble TRAIN receptor molecules that can compete with native TRAIN receptors for ligand binding according to the assays described herein can be selected as TRAIN receptor blocking agents.

A soluble TRAIN receptor comprising amino acid sequences selected form those shown herein may be attached to one or more heterologous protein domains ("fusion domains") to increase the in vivo stability of the receptor fusion protein, or to modulate its biological activity or localization.

Preferably, stable plasma proteins—which typically have a half-life greater than 20 hours in the circulation of a mammal—are used to construct the receptor fusion proteins. Such plasma proteins include but are not limited to: immunoglobulins, serum albumin, lipoproteins, apolipoproteins and transferrin. Sequences that can target the soluble receptors to a particular cell or tissue type may also be attached to the receptor ligand binding domain to create a specifically localized soluble receptor fusion protein.

All or a functional fragment of the TRAIN receptor extracellular region comprising the TRAIN receptor ligand binding domain may be fused to an immunoglobulin constant region like the Fc domain of a human IgG1 heavy chain. Soluble receptor—IgG fusions proteins are common immunological reagents and methods for their construction are well known in the art. (see, e.g. U.S. Pat. No. 5,225,538).

A functional TRAIN-R ligand binding domain may be fused to an immunoglobulin (Ig) Fc domain derived from an immunoglobulin class or subclass other than IgG1 . The Fc domains of antibodies belonging to different Ig classes or subclasses can activate diverse secondary effector functions. Activation occurs when the Fc domain is bound by a cognate Fc receptor Secondary effector functions include the ability to activate the complement system, to cross the placenta and to bind various microbial proteins. The properties of the different classes and subclasses of immunoglobulins are described in the art.

Activation of the complement system initiates cascades of enzymatic reactions that mediate inflammation. The products of the complement system have a variety of functions, including binding of bacteria, endocytosis, phagocytosis, cytotoxicity, free radical production and solubilization of immune complexes.

The complement enzyme cascade can be activated by the Fc domains of antigen-bound IgG1, IgG3 and Ig M antibodies. The Fc domain of IgG2 appears to be less effective, and the Fc domains of IgG4, IgA, IgD and IgE are ineffective at activating complement. Thus one can select an Fc domain based on whether its associated secondary effector functions are desirable for the particular immune response or disease being treated with the receptor-fusion protein.

It if would be advantageous to harm or kill the TRAIN ligand bearing target cell, one could, for example, select an especially active Fc domain (IgG1) to make the fusion protein. Alternatively, if it would be desirable to target the TRAIN receptor-FC fusion to a cell without triggering the complement system, an inactive IgG4 Fc domain could be selected.

Mutations in Fc domains that reduce or eliminate binding to Fc receptors and complement activation have been described in the art. These or other mutations can be used, alone or in combination to optimize the activity of the Fc domain used to construct the TRAIN receptor-Fc fusion protein.

One skilled in the art will appreciate that different amino acid residues forming the junction point of the receptor-Ig fusion protein may alter the structure, stability and ultimate biological activity of the soluble TRAIN receptor fusion protein. One or more amino acids may be added to the C-terminus of the selected TRAIN receptor fragment to modify the junction point whit the selected fusion domain.

The N-terminus of the TRAIN receptor fusion protein may also be varied by changing the position at which the selected TRAIN receptor DNA fragment is cleaved at its 5' end for insertion into the recombinant expression vector. The stability and activity of each TRAIN receptor fusion protein may be tested and optimized using routine experimentation and the assays for selecting blocking agents described herein.

Using the TRAIN receptor binding domain sequences within the extracellular domain as shown herein, amino acid sequence variants may also be constructed to modify the affinity of the soluble TRAIN receptor molecules for their ligands. The soluble molecules of this invention can compete for binding with endogenous receptors. It is envisioned that any soluble molecule comprising a TRAIN receptor ligand binding domain that can compete with native receptors for ligand binding is a receptor blocking agent that falls within the scope of the present invention.

In other embodiments of this invention, antibodies directed against the TRAIL and TRAIN receptors (anti-TRAIN-R abs) function as receptor blocking agents. The antibodies of this invention can be polyclonal or monoclonal and can be modified to optimize their ability to block TRAIN-R signaling, their bioavailability, stability or other desired traits.

Polyclonal antibody sera directed against TRAIN-R are prepared using conventional techniques by injecting animals such as goats, rabbits, rats, hamsters or mice subcutaneously with TRAIN-R-Fc fusion protein in Freund's adjuvant, followed by booster intraperitoneal or subcutaneous injection in incomplete Freund's. Polyclonal antisera containing the desired antibodies directed against the TRAIN receptors can then be screened by conventional immunological procedures.

Various forms of anti-TRAIN-R abs can also be made using standard recombinant DNA techniques. For example, "chimeric" antibodies can be constructed in which the antigen binding domain from an animal antibody is linked to a human constant domain. Chimeric antibodies reduce the observed immunogenic responses elicited by animal antibodies when used in human clinical treatments.

In addition, recombinant "humanized" antibodies which can recognize the TRAIN-R can be synthesized. Human antibodies are chimeras comprising mostly human IgG sequences into which the regions responsible for specific antigen-binding have been inserted. (e.g. WO 94/04679). Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (inter species) sequences in human antibodies, and are less likely to elicit immune responses in the mammal being treated.

Construction of different classes of recombinant anti-TRAIN-R antibodies can also be accomplished by making chimeric or humanized antibodies comprising the anti-R variable domains and human constant domains isolated from different classes of immunoglobulins. For example, anti-TRAIN-R IgM antibodies with increased antigen binding site valencies can be recombinantly produced by cloning the antigen binding site into vectors carrying the human μ chain constant regions.

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modeling.

It may be desirable to increase or decrease the affinity of anti-TRAIN-R antibodies for the receptors depending on the targeted tissue type or the particular treatment schedule envisioned. For example, it may be advantageous to treat a patient with constant levels of anti-Receptor antibodies with reduced ability to signal through the pathway for semi-prophylactic treatments. Likewise, inhibitory anti-TRAIN-R antibodies with increased affinity for the receptors may be advantageous for short term treatments.

The claimed invention in yet other embodiments encompasses pharmaceutical compositions comprising an effective amount of a TRAIN-R blocking or activating agent, and pharmaceutically acceptable carriers. The compositions of the invention will be administered at an effective dose to treat the particular clinical condition addressed. Determination of a preferred pharmaceutical formulation and a therapeutically efficient dose regiment for a given application is well within the skill of the art taking into consideration for example, the condition and weight of the patient, the extent of desired treatment and the tolerance of the patient for the treatment. Doses of about 1 mg/kg of a soluble TRAIN-R are expected to be suitable starting points for optimizing treatment dosages.

Determination of a therapeutically effective dose can also be assessed by performing in vitro experiments that measure the concentration of the blocking or activating agent. The binding assays described herein are useful, as are other assays known in the art.

Administration of the soluble activating or blocking agents of the invention, alone or in combination, including isolated and purified forms, their salts, or pharmaceutically acceptable derivative thereof may be accomplished using any of the conventionally accepted modes of administration of agents which exhibit immunosuppressive activity.

EXAMPLES

Generation of Soluble Receptor Forms:

To form an receptor inhibitor for use in man, one requires the human receptor cDNA sequence of the extracellular domain. If the mouse form is known, human cDNA libraries can be easily screened using the mouse cDNA sequence and such manipulations are routinely carried out in this area. With a human cDNA sequence, one can design oligonucleotide primers to PCR amplify the extracellular domain of the receptor in the absence of the transmembrane and intracellular domains. Typically, one includes most of the amino acids between the last disulfide linked "TNF domain" and the transmembrane domain. One could vary the amount of "stalk" region included to optimize the potency of the resultant soluble receptor. This amplified piece would be engineered to include suitable restriction sites to allow cloning into various C-terminal Ig fusion chimera vectors. Alternatively, one could insert a stop signal at the 3' end and make a soluble form of the receptor without resorting to the use of a Ig fusion chimera approach. The resultant vectors can be expressed in most systems used in biotechnology including yeast, insect cells, bacteria and mammalian cells and examples exist for all types of expression. Various human Fc domains can be attached to optimize or eliminate FcR and complement interactions as desired. Alternatively, mutated forms of these Fc domains can be used to selectively remove FcR or complement interactions or the attachment of N-linked sugars to the Fc domain which has certain advantages.

Generation of Agonistic or Antagonistic Antibodies:

The above described soluble receptor forms can be used to immunize mice and to make monoclonal antibodies by conventional methods. The resultant mAbs that are identified by ELISA methods can be further screened for agonist activity either as soluble antibodies or immobilized on plastic in various in vitro cellular assays. Often the death of the HT29 cell line is a convenient system that is sensitive to signaling through many TNF receptors. If this line does not possess the receptor of interest, that full length receptor can be stably transfected into the HT29 line to now allow the cytotoxicity assay to work. Alternatively, such cells can be used in the Cytosensor apparatus to assess whether activation of the receptor can elicit a pH change that is indicative of a signaling event. TNF family receptors signal well in such a format and this method does not require one to know the actual biological events triggered by the receptor. The agonistic mAbs would be "humanized" for clinical use. This procedure can also be used to define antagonistic mAbs. Such mAbs would be defined by the lack of agonist activity and the ability to inhibit receptor-ligand interactions as monitored by ELISA, classical binding or BIAcore techniques. Lastly, the induction of chemokine secretion by various cells in response to an agonist antibody can form a screening assay.

Screening for Inhibitors of the Receptor-Ligand Interaction:

Using the receptor-Ig fusion protein, one can screen either combinatorial libraries for molecules that can bind the receptor directly. These molecules can then be tested in an ELISA formatted assay using the receptor-Ig fusion protein and a soluble form of the ligand for the ability to inhibit the receptor-ligand interaction. This ELISA can be used directly to screen various natural product libraries etc. for inhibitory compounds. The receptor can be transfected into a cell line such as the HT29 line to form a biological assay (in this case cytotoxicity) that can then form the screening assay.

It will be apparent to those skilled in the art that various modifications and variations can be made in the polypeptides, compositions and methods of the invention without departing from the spirit or scope of the invention. Thus, it is intended that the present invention cover the modifications and variations of this invention provided that they come within the scope of the appended claims and their equivalents.

Human TRAIN Receptor Identification:

Human TRAIN-R was cloned from two cDNA sequences. The first sequence (hTrainR) SEQ ID NO. 7 is a composite of two overlapping lambda gt10 clones (GJ159 and GJ158) from a Clontech Human adult lung cDNA library. The composite sequence in SEQ. ID. NO. 7 is 2185 nucleotides in length and encodes a 417 amino acid protein (SEQ. ID. NO.3) which has a signal sequence, a 140 amino acid extracellular domain, a transmembrane domain and a 227 amino acid intracellular domain and a stop codon. The includes another 1200 bp. The extracellular domain of human TRAIN-R encodes three TNF receptor like domains (it appears to be missing domain 1 when compared to TNF-R). The sequence in SEQ. ID. NO. 3 is 19% identical to that of low affinity nerve growth factor (LNGFR) and 24% identical to Tramp/Lard4/Ws1/Dr3, both of which are members of the TNF family.

Human TRAIN-R was also cloned from a second sequence subclone of a lambda gt10 cDNA (GJ156, a 790 bp subclone). The resulting sequence is shown in SEQ. ID. NO. 8. It contains intron sequence, an exon encoding the Carboxy-terminal 30 amino acids of a secreted form of human TrainR, a stop codon and a 3'UTR. The 30 amino acids in the exon sequence were 100% homologous to the murine C-term secreted form (short form of murine Train Receptor).

Two predominant messages are observed 5 kb and 0.5 kb.

---

We claim:

1. An isolated nucleic acid encoding a TRAIN receptor polypeptide, wherein said nucleic acid comprises the nucleotide sequence of SEQ ID NO: 7.

2. An isolated nucleic acid encoding a TRAIN receptor polypeptide, wherein said polypeptide comprises an amino acid sequence selected from the group consisting of:
   (a) SEQ ID NO: 3;
   (b) SEQ ID NO: 9; and
   (c) amino acid residues 26 to 417 of SEQ ID NO:3;
   (d) amino acid residues 1 to 173 of SEQ ID NO:3;
   (e) amino acid residues 26 to 173 of SEQ ID NO:3;
   (f) amino acid residues 1 to 190 of SEQ ID NO:3;
   (g) amino acid residues 26 to 190 of SEQ ID NO:3;
   (h) amino acid residues 174 to 190 of SEQ ID NO:3;
   (i) amino acid residues 174 to 417 of SEQ ID NO:3; and
   (j) amino acid residues 191 to 417 of SEQ ID NO:3.

3. A vector comprising the isolated nucleic acid of claim 1, wherein said nucleic acid is operatively linked to an expression control sequence capable of expressing said isolated nucleic acid in a cell.

4. An isolated cell transformed with the vector of claim 3, wherein said cell expresses said TRAIN receptor polypeptide.

5. A vector comprising the isolated nucleic acid of claim 2, wherein said nucleic acid is operatively linked to an expression control sequence capable of expressing said isolated nucleic acid in a cell.

6. An isolated cell transformed with the vector of claim 5, wherein said cell expresses said TRAIN receptor polypeptide.

7. A method of producing a TRAIN receptor polypeptide, comprising the steps of:
   (a) constructing a vector comprising an isolated nucleic acid having the nucleic acid sequence of SEQ ID NO:7 operatively linked to an expression control sequence;
   (b) transforming a host cell with said vector, thereby creating a transformed cell; and
   (c) growing said transformed cell in cell medium, whereby said TRAIN receptor polypeptide is expressed.

8. The method according to claim 7, further comprising the step of isolating said TRAIN receptor polypeptide from said cell medium.

9. The method according to claim 7, wherein said host cell is selected from the group consisting of yeast, insect, bacterial and mammalian cells.

10. The method according to claim 7, wherein said vector comprises a fragment of said isolated DNA encoding a polypeptide having an amino acid sequence selected from the group consisting of:
(a) SEQ ID NO: 3;
(b) SEQ ID NO: 9; and
(c) amino acid residues 26 to 417 of SEQ ID NO:3;
(d) amino acid residues 1 to 173 of SEQ ID NO:3;
(e) amino acid residues 26 to 173 of SEQ ID NO:3;
(f) amino acid residues 1 to 190 of SEQ ID NO:3;
(g) amino acid residues 26 to 190 of SEQ ID NO:3;
(h) amino acid residues 174 to 190 of SEQ ID NO:3;
(i) amino acid residues 174 to 417 of SEQ ID NO:3; and
(j) amino acid residues 191 to 417 of SEQ ID NO:3.

11. The method according to claim 10, further comprising the step of isolating said TRAIN receptor polypeptide from said cell medium.

12. The method according to claim 10, wherein said host cell is selected from the group consisting of yeast, insect, bacterial and mammalian cells.

* * * * *